United States Patent [19]

Greenleaf et al.

[11] Patent Number: 4,829,430

[45] Date of Patent: May 9, 1989

[54] METHOD FOR REDUCING ARTIFACTS IN ULTRASOUND BACKSCATTER TOMOGRAPHY

[75] Inventors: James F. Greenleaf, Rochester, Minn.; Juha T. Ylitalo, Oulu, Finland

[73] Assignee: Mayo Foundation for Medical Education and Research, Rochester, Minn.

[21] Appl. No.: 120,046

[22] Filed: Nov. 13, 1987

[51] Int. Cl.$^4$ .............................................. G06F 15/42
[52] U.S. Cl. ............................... 364/413.25; 358/111; 378/901
[58] Field of Search ..................... 364/414; 378/90, 99, 378/901; 358/111

[56] References Cited

U.S. PATENT DOCUMENTS

| | | | |
|---|---|---|---|
| 4,549,265 | 10/1985 | Deckers et al. | 364/414 |
| 4,680,709 | 7/1987 | Srinivasan et al. | 364/414 |
| 4,707,822 | 11/1987 | Hopkinson et al. | 364/414 |

OTHER PUBLICATIONS

"A Characterization of Wavefront Distortion for Analysis of Ultrasound Diffraction Measurements Made Through an Inhomogeneous Medium", Waag et al., *IEEE Transactions on Sonics and Ultrasonics*, vol. SU-32, No. 1, pp. 36–48, Jan. 1985.
"Tomographic Imaging of Ultrasonic Reflectivity with Correction for Acoustic Speed Variations", Kim et al., *Ultrasonic Imaging*, vol. 6, No. 3, pp. 304–312, Jul. 1984.
"Method of Data Reduction for Accurate Determination of Acoustic Backscatter Coefficients", Madsen et al., *J. Acoust. Soc. Am.*, 76(3), pp. 913–923, Sep. 1984.
"B–Mode Registration: A New Procedure for Analyzing Errors", Insana and Goldstein, *Med. Phys.*, 7(6), pp. 644–654, Nov./Dec. 1980.
"Tests of the Accuracy of A Data Reduction Method for Determination of Acoustic Backscatter Coefficients", *J. Acoust. Soc. Am.*, 79(5), Insana et al., pp. 1230–1236, May 1986.
"Analysis of Ultrasound Image Texture Via Generalized Rician Statistics", *Optical Engineering*, vol. 25, No. 6, Insana et al., pp. 743–748, Jun. 1986.
"Unified Approach to the Detection and Classification of Speckle Texture in Diagnostic Ultrasound", Wagner et al., *Optical Eng.*, vol. 25, No. 6, pp. 738–742, Jun. 1986.
"Quantitative Estimation of Liver Attenuation and Echogenicity: Normal State Versis Diffuse Liver Disease", Garra et al., *Radiology*, vol. 162, No. 1, pp. 61–67, Jan. 1987.
"Improvements in the Spectral Difference Method for Measuring Ultrasonic Attenuation", Insana et al., *Ultrasonic Imaging*, vol. 5, pp. 331–345, 1983.
"Acoustic Backscattering From Ultrasonically Tissue-like Media", Insana et al., *Med. Phys.* 9(6), pp. 848–855, Nov./Dec. 1982.
"Ultrasonically Tissue–Mimicking Liver Including the Frequency Dependence of Backscatter", Madsen et al., *Med. Phys.*, vol. 9, No. 5, pp. 703–710, Sep./Oct. 1982.

*Primary Examiner*—A. D. Pellinen
*Assistant Examiner*—Jeffrey A. Gaffin
*Attorney, Agent, or Firm*—Quarles & Brady

[57] ABSTRACT

Sets of raw profile data are acquired from a subject using an ultrasound reflective mode tomographic scan. This raw data is corrected for errors due to inhomogeneities in the speed of sound and an image is reconstructed from the corrected data set. The corrections are made by shifting each set of raw profile data such that a prominent signal therein aligns with a corrective sinusoid which indicates the ideal location of the prominent signal in each set of profile data.

6 Claims, 2 Drawing Sheets

METHOD FOR REDUCING ARTIFACTS IN ULTRASOUND BACKSCATTER TOMOGRAPHY

BACKGROUND OF THE INVENTION

The field of the invention is acoustical imaging and, in particular, ultrasound imaging using reflection mode computerized tomography.

There are a number of modes in which ultrasound can be used to produce images of objects. The ultrasound transmitter may be placed on one side of the object and the sound transmitted through the object to the ultrasound receiver which is placed on the other side ("transmission mode"). With transmission mode methods, an image may be produced in which the brightness of each pixel is a function of the amplitude of the ultrasound that reaches the receiver ("attenuation" mode), or the brightness of each pixel is a function of the time required for the sound to reach the receiver ("time-of-flight" or "speed of sound" mode). In the alternative, the receiver may be positioned on the same side of the object as the transmitter and an image may be produced in which the brightness of each pixel is a function of the amplitude or time-of-flight of the ultrasound which is reflected from the object back to the receiver ("refraction", "backscatter" or "echo" mode). The present invention is a backscatter method for producing ultrasound images.

There are a number of well known backscatter methods for acquiring ultrasound data. In the so-called "A-scan" method, an ultrasonic pulse is directed into the object by the transducer and the amplitude of the reflected sound is recorded over a period of time. The amplitude of the echo signal is proportional to the scattering strength of the refractors in the object and the time delay is proportional to the range of the refractors from the transducer. In the so-called "B-scan" method, the transducer transmits a series of ultrasonic pulses as it is scanned across the object along a single axis of motion. The resulting echo signals are recorded as with the A-scan method and either their amplitude or time delay is used to modulate the brightness of pixels on a display. With the B-scan method, enough data are acquired from which an image of the refractors can be reconstructed.

In the so-called C-scan method, the transducer is scanned across a plane above the object and only the echoes reflecting from the focal depth of the transducer are recorded. The sweep of the electron beam of a CRT display is synchronized to the scanning of the transducer so that the x and y coordinates of the transducer correspond to the x and y coordinates of the image.

Computer tomography has found widespread use in the medical field since its discovery by Hounsfield in 1973. Tomography is commonly implemented by revolving an X-ray source and an opposing X-ray detector about the patient. A series of measurement are made from different angles as the source and detector revolve about the patient. The resulting X-ray absorption data are used to reconstruct an image which is a cross sectional view through a single plane. The image is typically reconstructed using a Fourier transform or filtered back propogation method. Although transmission mode ultrasound tomography has been successfully implemented, refraction mode ultrasound tomography has not been successful due to variations in the speed of sound as the transmitter and receiver are revolved around the patient.

SUMMARY OF THE INVENTION

The present invention is a method for practicing backscatter ultrasound tomography and, in particular, a method for correcting the acquired data for errors caused by speed of sound variations. The method includes the steps of acquiring a set of profile data using an ultrasound backscatter mode tomographic scan; reconstructing a raw image from this acquired set of data; locating an indentifiable point in this raw image; calculating a corrective sinusoid which indicates the ideal location of the identifiable point in each acquired data profile; correcting each data profile in the set by shifting the data profile amount necessary to place actual signal corresponding to the identifiable point at the ideal location; and reconstructing an image using the corrected set of profile data.

A general object of the invention is to correct data acquired using backscatter mode ultrasound tomography. As the acoustic transducer revolves around the patient, the ultrasonic pulses which it produces travel through different tissues on their paths to and from the refracting objects. The speed of sound typically varies in different tissue types and the resulting echo signal which indicates the profile of the refractors in the patient will vary as a function of viewing angle. The reconstruction algorithms used in tomography assume that the sound velocity is uniform from all viewing angles, and as a result, the refracting objects in the reconstructed image are blurred by sound velocity inhomogeneities. The present invention shifts each data profile by an amount of time which corrects for the sound velocity inhomogeneities and the image which is reconstructed from the corrected set of profile data is not blurred.

A more specific object of the invention is to provide an easily implemented method for correcting ultrasound refraction mode tomographic data for inhomogeneities in the speed of sound. The echo signal from the brightest refractor in the region of interest is located in each profile. In a media which transmits ultrasound at a homogeneous velocity, and assuming the refractor is not at the center of rotation of the transducer, the time at which this peak echo signal is received will vary sinusoidally as the viewing angle of the transducer progresses around the patient. To the extent this is not the case, the time error is due to changes in sound velocity. Accordingly, by shifting each data profile such that its peak echo is aligned with the ideal sine wave, the entire data set can be easily corrected for errors due to sound velocity inhomogeneity.

The foregoing and other objects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims herein for interpreting the scope of the invention.

DESCRIPTION OF THE PREFERRED EMBODIMENT

Figure 1A:
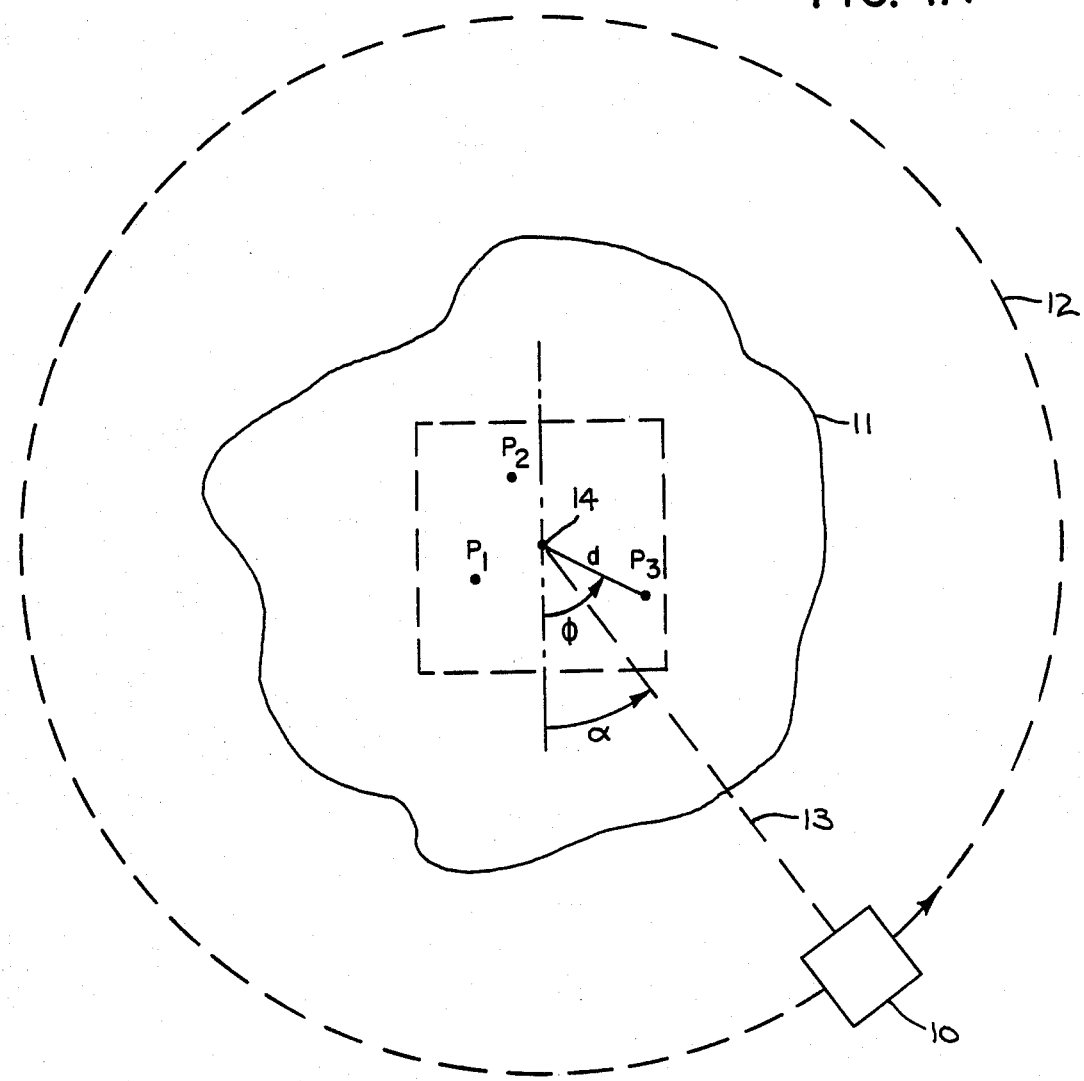
FIG. 1A is a schematic representation of the data acquisition step which forms part of the present invention.

Referring particularly to FIG. 1, an ultrasonic transducer 10 is mounted to revolve around a subject to be studied 11 along a circular path indicated by dashed line 12. A 3.5 megaHertz focused transducer is used to form synthetically a parallel beam indicated by dashed line 13 which has a width of 9.7 millimeters. A tomographic scanner such as that described in an article, "A Clinical Prototype Ultrasonic Transmission Tomographic Scanner", by J. F. Greenleaf, J. J. Gisvold and R. C. Bahn, which appeared in *Acoustical Imaging*, Vol, 12, pp. 579–587, published in 1982 by Plenum Publishing Corporation is used for this purpose. At each of 200 equally spaced positions around the circular path 12, the transducer 10 sends a narrow plane wave into the subject 11 which is directed towards the center of revolution 14. The ultrasonic sound which is refracted back to the transducer 10 by the object 11 is received, coherently sampled, and digitized at a 10 megaHertz rate. The resulting date are stored as a 128 sample data profile. A complete set of 200 such data profiles are acquired and stored as the transducer 10 revolves completely around the subject 11.

Figure 1B:
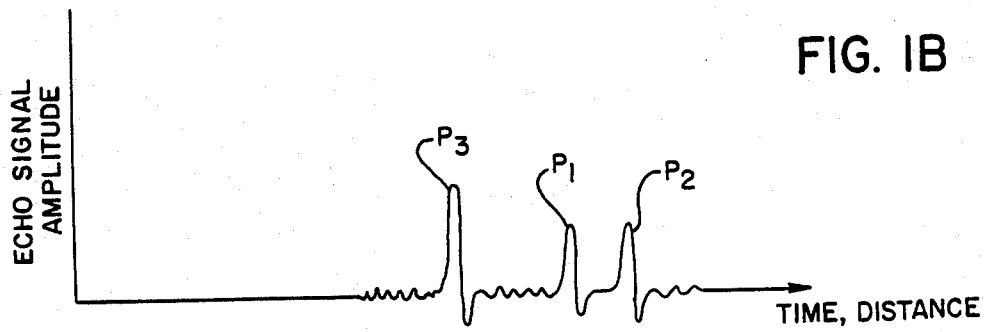
FIG. 1B is a schematic representation of a single data profile which is acquired during the data acquisition of FIG. 1A.

A data profile for one orientation, or viewing angle, of the transducer 10 is shown in FIG. 1B. The horizontal axis represents time following the transmission of the ultrasonic pulse and the vertical axis is the amplitude of the refracted signal. Those skilled in the art will recognize the data profile as the same data obtained using an A-scan method. In the example of FIG. 1A, three refractor points $P_1$, $P_2$, and $P_3$ dominate the subject and these appear in the data profile as the three peaks $P_1$, $P_2$ and $P_3$. If the velocity of sound is uniform along the path 13 of the ultrasonic pulse, the spacing between the peaks in the data profile also indicates the distance between them as measured in the direction of the pulse path 13. It can be appreciated by those skilled in the art that the peaks $P_1$–$P_3$ in the data profile change position and order as the transducer 10 revolves around the subject and the viewing angle $\alpha$ of the pulse path 13 changes.

The complete set of raw digitized data may be employed to reconstruct a raw image using well known tomographic methods. In the preferred embodiment, a filtered back propogation construction method such as that described in *Image Reconstruction from Projections: The Fundamentals of Computerized Tomography*, by G. T. Herman and published in 1980 by Academic Press, is used for image reconstruction. In the alternative, the Fourier slice theorem with direct Fourier inversion may be applied, assuming a straight-line approximation for the A-line projections. Regardless of the reconstruction method used, the inhomogeneities in the speed of sound in tissues surrounding the region being imaged, will distort the measured refraction time. This distortion is usually seen as a blurring of point reflectors, although it may also be manifested as a ghost or blurring to one side of the reflector.

In accordance with the present invention, the coordinates of a distinctive refractor point in the raw image is selected. The brightest point is preferred, since it produces the highest peak in each of the data profiles and is easily located therein. The position of the selected refractor is expressed as a distance d from the center of rotation and an angle $\phi$ which is the point's relative angle to the starting point of the circular transducer scan. These dimensions are shown in FIG. 1A, where refractor $P_3$ is the brighest point in the raw image as shown in the data profile of FIG. 1B.

The location of the brightest point is then used to calculate a clean, or ideal, sinusoid which corresponds to the selected point.

$$S(i) = d \cos(\phi - \alpha)$$

Where:
$\alpha = 2\pi i/N$, an angle the transducer 10 forms relative to the starting point of the scan, where i is the data profile number and N is the total number of data profiles which were acquired.

In the preferred embodiment described herein, the transducer 10 revolves 360° around the subject. There are tomographic methods, however, which do not require a complete revolution and the present invention may be employed with them as well. In such case, the constant "$2\pi$" in the above equation will, of course, be different.

Figure 2A:
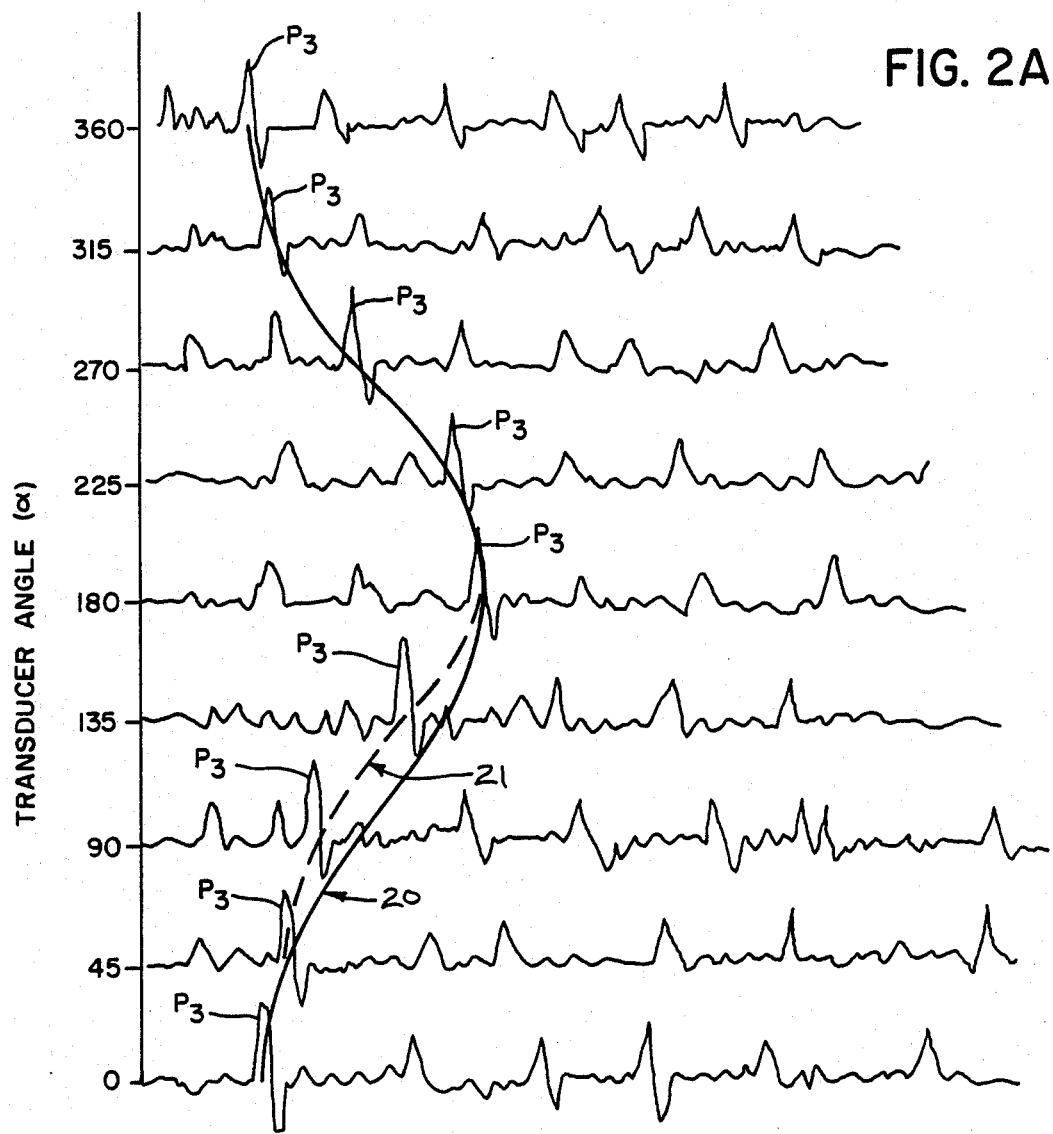
FIG. 2A is a schematic representation of the set of data profiles acquired during the data acquisition of FIG. 1A showing how the data is corrected.

Referring particularly to FIG. 2A, the calculated sinusoid is shown as the solid line 20 which has been superimposed over representative data profiles in the complete raw data set. Ideally, the peak signal in each data profile, represented by the peak $P_3$, should align perfectly with this calculated sinusoid. However, as illustrated by the data profiles at angles of 90° and 135°, the signal peaks $P_3$ occur before the sinusoid 20 as indicated by dashed line 21. This indicates that the speed of sound in tissues through which the ultrasound pulse traveled when the transducer 10 was located at these viewing angles was faster than the speed of sound in other tissues surrounding the region of interest. As a result, the refracted signals were received at the transducer 10 sooner, and the entire data profile is shifted to the left along the time axis. The amount of this shift in the data profile is the time difference between the peak $P_3$ and the sinusoid S(i), and it is this shift which produces the artifacts in the raw image which are removed by the present invention. The location of the peak $P_3$ may be determined by examining the digitized profile data for the maximum amplitude, or in the alternative, the data profiles may be rectified and filtered before this examination is performed.

Accordingly, each data profile in the raw data set is corrected by shifting it either left or right along the time axis by an amount necessary to align its peak signal with the calculated sinusoid S(i). In the example of FIG. 2A, therefore, the data profiles corresponding to the viewing angles 90° and 135° are shifted to the right to align their peaks $P_3$ with the sinusoid 20. Other data profiles between and around these two angles are also shifted to the right, but many of the data profiles remain unchanged. The amount and direction of the corrections to the raw data will, of course, depend on the speed variations which occur in the tissues surrounding the refractor point $P_3$.

Figure 2B:
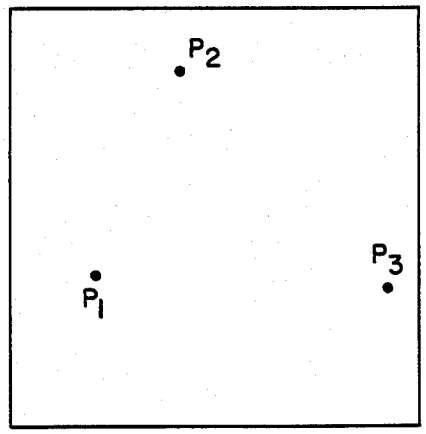
FIG. 2B is the image which is reconstructed using the corrected data set.

Appendix A is a source code listing of the Fortran program which is employed to correct the raw data in accordance with the present invention. The corrected set of data profiles is then used to reconstruct the final image which is shown in FIG. 2B. The reconstruction is performed in exactly the same manner as that used to reconstruct the raw image as described above. Of course, however, by using the corrected data set the artifacts such as blurring and ghosting due to inhomogeneities are removed from the image.

A variation of the invented method may be necessary in instances where no single refractor produces a suitable echo throughout the entire range of viewing angles. In such cases, it may be necessary to calculate ideal sinusoids for more than one refractor point. When the data profiles are then corrected, the peaks in the data profile produced by any of the calculated refractors may be detected and the needed correction may be determined by comparing it with the corresponding ideal sinusoid. Thus, if the peak for one refractor is not present in a particular data profile, another peak and the corresponding ideal sinusoid may be used. It should also be apparent that when correction values are calculated using more than one refractor and ideal sinusoid, these can be averaged by well known techniques to improve further the quality of the reconstructed image.

It should be apparent to those skilled in the art that many variations are possible without departing from the spirit of the invention. There are numerous methods and apparatus available for acquiring ultrasound backscatter tomographic data from a subject. There are also numerous methods and apparatus available for reconstructing an image from such tomographic data sets. The present invention is a method for correcting such tomographic data sets to eliminate artifacts in the reconstructed images caused by inhomogeneities in sound speed.

APPENDIX A

```
1              SUBROUTINE CORREC(NV,ISHI,NLP,FREQ,FSAMP)
2       C
3       C
4       C  THIS SUBROUTINE CORRECTS THE RAW DATA
5       C  IT FOLLOWS THE MAX DATA VALUE THROUGH
6       C  ALL PROJECTIONS
7       C
8       C
9       C
10      C
11             DIMENSION A(128,256),FSIM(300,128)
12             DIMENSION FF(300),FF2(128),LOSTI(128),CMAX(300)
13             DIMENSION F7(128),JA(300),JB(300),JC(300),JDIF(300)
14             COMMON A,FSIM
15      C
16             PII=3.14159
17      C
18      C **  WINDOW LENGTH NWIN:
19             NWIN=6
20      C
21      C  FIND MAX VALUES OF EACH PROJECTION
22      C
23             IF(ISHI.EQ.333) MRETUR=1
24             INUM=0
25             JDIFCA=0
26             CMAXCA=0
27             CMXX=0
28      C
29      C ****
30      C
31             DO 10 I=1,NV
32               DO 2 J=1,128
33                 P0=J*FREQ*2*PII/FSAMP
34                 PH=P0-INT(P0/(2*PII))*2*PII
35                 SR=FSIM(I,J)*COS(PH)
36                 SI=FSIM(I,J)*SIN(PH)
37                 F7(J)=SQRT(SR*SR+SI*SI)
38      2        CONTINUE
39      C
40               DO 4 J=1,128-NLP-1
41                 DO 3 JJ=1,NLP-1
```

```
42                    JJJ=J+JJ
43    C               IF(JJJ.GT.128) JJJ=128
44                    F7(J)=F7(J)+F7(JJJ)
45    3           CONTINUE
46                F7(J)=F7(J)/NLP
47    4       CONTINUE
48    C
49            CX1=0
50            DO 5 J=1,128
51            IF(F7(J).GT.CX1) THEN
52            CX1=F7(J)
53            IF(CX1.GT.CMXX) CMXX=CX1
54            JDIF(I)=J
55            CMAX(I)=F7(J)
56            ENDIF
57    5       CONTINUE
58    10   CONTINUE
59         GO TO 1200
60    C
61    C
62         DO 22 I=1,NV
63         CX1=0
64         CX2=0
65         CX3=0
66         JX=1
67            DO 11 J=1,128
68            IF(ABS(FSIM(I,J)).GT.CX1) THEN
69            JA(I)=J
70            JX=J
71            CX1=ABS(FSIM(I,J))
72            IF(CX1.GT.CMXX) CMXX=CX1
73            ELSE IF(ABS(FSIM(I,J)).GT.CX2.AND.(J-JA(I)).GT.2) THEN
74               JB(I)=J
75               CX2=ABS(FSIM(I,J))
76                  ELSE IF(ABS(FSIM(I,J)).GT.CX3.AND.(J-JA(I)).GT.2
77    1                    .AND.(J-JB(I)).GT.2) THEN
78               JC(I)=J
79               CX3=ABS(FSIM(I,J))
80            ENDIF
81    C
82            CMAX(I)=CX1
83    C       JDIF(I)=JX
84    11      CONTINUE
85    C
86         IF(JA(I).GT.JB(I)) THEN
87            IF(JB(I).GT.JC(I)) THEN
88            JBB=JA(I)
89            JA(I)=JC(I)
90            JC(I)=JBB
91            ELSE IF(JA(I).GT.JC(I)) THEN
92               JBB=JA(I)
93               JBC=JC(I)
94               JA(I)=JB(I)
95               JB(I)=JBC
96               JC(I)=JBB
97               ELSE
98               JBB=JA(I)
99               JA(I)=JB(I)
100              JB(I)=JBB
```

```
101                         ENDIF
102                      ELSE IF(JB(I).GT.JC(I)) THEN
103                         JBB=JA(I)
104                         JBC=JB(I)
105                         JA(I)=JC(I)
106                         JB(I)=JBB
107                         JC(I)=JBC
108                      ELSE
109                             JBB=JB(I)
110                             JB(I)=JC(I)
111                             JC(I)=JBB
112                      ENDIF
113      C
114      C
115      22       CONTINUE
116      C
117               S1=0
118               S2=0
119               S3=0
120               DO 226 I=1,NV
121               S1=S1+ABS(FSIM(I,JA(I)))
122               S2=S2+ABS(FSIM(I,JB(I)))
123               S3=S3+ABS(FSIM(I,JC(I)))
124      226      CONTINUE
125      C
126               IF(S1.GT.S2) THEN
127                  IF(S1.GT.S3) THEN
128                     SX=S1
129                     JXX=JA(1)
130                  ELSE
131                     SX=S3
132                     JXX=JC(1)
133                  ENDIF
134               ELSE
135                  IF(S2.GT.S3) THEN
136                     SX=S2
137                     JXX=JB(1)
138                  ELSE
139                     SX=S3
140                     JXX=JC(1)
141                  ENDIF
142               ENDIF
143      C
144               JSTART=JXX
145               SXAVE=SX/NV
146      C
147               JS=0
148               DO 1101 I=1,12
149               C1=ABS(FSIM(I,JA(I)))
150               C2=ABS(FSIM(I,JB(I)))
151               C3=ABS(FSIM(I,JC(I)))
152               IF(C1.GT.C2 .AND. C1.GT.C3) JZ=JA(I)
153               IF(C2.GT.C1 .AND. C2.GT.C3) JZ=JB(I)
154               IF(C3.GT.C1 .AND. C3.GT.C2) JZ=JC(I)
155               JS=JS+JZ
156      1101     CONTINUE
157      C
158               JDIF(1)=JS/12
```

```
159        C
160                  DO 1121 I=1,NV
161                     DO 1111 I2=1,NWIN-1
162                     I3=I+I2
163                     JU1=JA(I3)-JDIF(I)
164                     JU2=JB(I3)-JDIF(I)
165                     JU3=JC(I3)-JDIF(I)
166        C
167                     IF(JU1.LT.JU2 .AND. JU1.LT.JU3) JU=JA(I3)
168                     IF(JU2.LT.JU1 .AND. JU2.LT.JU3) JU=JB(I3)
169                     IF(JU3.LT.JU1 .AND. JU3.LT.JU2) JU=JC(I3)
170        C
171                     IF((JU-JDIF(I)).LT.3) THEN
172                     JDIF(I3)=JU
173                     ELSE
174                     JDIF(I3)=0
175                     ENDIF
176        1111         CONTINUE
177        C
178                     IF(JDIF(I+1).EQ.0) JDIF(I+1)=JDIF(I)
179        1121      CONTINUE
180        C
181        1200      DO 1454 I=1,NV
182                  JDIFCA=JDIFCA+JDIF(I)
183                  CXC=ABS(FSIM(I,JDIF(I)))/CMXX
184                  WRITE(4,15) I,JDIF(I),CXC
185        15        FORMAT(4H ***,2(I5),F9.1)
186        1454      CONTINUE
187        C         CMAXCA=CMAXCA+CMX
188        C
189                  CMAXCA=CMAXCA/NV
190                  CMAXMI=.3*CMAXCA
191                  JDIFCA=JDIFCA/NV
192                  ISHI=65-JDIFCA-NLP/2
193        C
194                  WRITE(5,23) ISHI
195        23        FORMAT(8H SHIFT**,I5)
196        C
197        C
198        C
199                  DO 24 J=1,128
200                  FF(J)=0
201        24        CONTINUE
202        C
203                  IF(ISHI.NE.0) THEN
204                  DO 28 I=1,NV
205                  JDIF(I)=JDIF(I)+ISHI
206                     DO 25 J=1,128
207                     J2=J+ISHI
208                     IF(J2.LT.1 .OR. J2.GT.128) THEN
209                        FSIM(I,J)=0
210                        GO TO 25
211                     ENDIF
212                     FF(J2)=FSIM(I,J)
213        25           CONTINUE
214                  DO 27 J=1,128
215                  FSIM(I,J)=FF(J)/CMXX
216        27        CONTINUE
```

```
217    28        CONTINUE
218              ENDIF
219    C
220              IF(MRETUR.EQ.1) RETURN
221    C
222              DO 45 I=1,NV-NWIN+1
223              LOS=0
224              DO 30 I1=1,NWIN-1
225              I2=I+I1-1
226              IF(JDIF(I2)-JDIF(I2+1) .GT. 3) LOS=LOS+1
227    30        CONTINUE
228    C
229              IF(LOS.EQ.0) GO TO 45
230              IF(LOS.EQ.1 .AND. I.EQ.1) THEN
231              CMAX(I)=0
232              INUM=INUM+1
233              LOSTI(INUM)=I
234              ELSE IF(LOS.EQ.1) THEN
235              GO TO 45
236              ENDIF
237    C
238              WRITE(5,811)
239    811       FORMAT(7H *LOST!)
240              JDFCA=0
241              DO 35 I2=I,I+NWIN-1
242              JDFCA=JDFCA+JDIF(I2)
243    35        CONTINUE
244              JDFCA=JDFCA/NWIN
245    C
246              DO 40 I2=I,I+NWIN-1
247              IF((JDIF(I2)-JDFCA).GT.15) THEN
248              CMAX(I2)=0
249              INUM=INUM+1
250              LOSTI(INUM)=I2
251              ENDIF
252    40        CONTINUE
253    C
254    45        CONTINUE
255    C
256    C
257                ILOST=INUM
258                WRITE(5,48) ILOST
259    48          FORMAT(19H LOSTED VIEWS *****:,I5)
260    C
261    C
262    C  INTERPOLATE LOSTED PROFILES
263    C
264              DO 77 I=1,ILOST
265              WRITE(5,34) I
266    34        FORMAT(7H ******,I5)
267              N=1
268              IF(LOSTI(I).EQ.1) THEN
269    50          IF(CMAX(LOSTI(I)+N).EQ.0) THEN
270                  N=N+1
271                  GO TO 50
272                ELSE
273                  DO 55 I2=1,N
274                  DO 55 J=1,128
```

```
275                         FSIM(I2,J)=FSIM(N+1,J)
276                         JDIF(I2)=JDIF(N+1)
277         55           CONTINUE
278                  ENDIF
279   C
280             ELSE
281   C
282                  N=1
283         60      IF(CMAX(LOSTI(I)+N).EQ.0) THEN
284                     N=N+1
285                     GO TO 60
286                  ELSE
287                     N2=N+LOSTI(I)
288                  ENDIF
289   C
290                  N=1
291         65      IF(CMAX(LOSTI(I)-N).EQ.0) THEN
292                     N=N+1
293                     GO TO 65
294                  ELSE
295                     N1=LOSTI(I)-N
296                  ENDIF
297   C
298                  J1=NINT((JDIF(N1)+JDIF(N2))*.5)
299   C
300                  DO 70 N=N1+1,N2-1
301                  DO 70 J=1,128
302                  J2=JDIF(N1)-J1+J
303                  IF(J2.LT.1 .OR. J2.GT.128) GO TO 70
304   C
305                  FSIM(LOSTI(N),J2)=FSIM(N2,J)
306                  JDIF(N)=J1
307   C
308         70      CONTINUE
309   C
310             ENDIF
311   C
312         77      CONTINUE
313   C
314   C
315   C  FIND THE DOMINANT MAX VALUE SINE FUNCTION
316   C
317                  WRITE(5,78)
318         78      FORMAT(19H FIND SINE CURVE***)
319             DO 80 J=1,NV
320             FF(J)=JDIF(J)-65
321                  WRITE(5,794) FF(J)
322        794      FORMAT(8H PRE FFT,F9.1)
323         80     CONTINUE
324   C
325   C  ***
326             MPEAKS=0
327             NZEROS=0
328             JSUM=0
329             MDER0=0
330   C
331   C
332             DERMAX=0
```

```
333     C ***
334             JDER1=0
335             JDER2=0
336             JDER3=0
337             LDER1=0
338             LDER2=0
339             LDER3=0
340             N=0
341             DO 420 J=1,NV-1
342             DER=FF(J+1)-FF(J)
343             IF(ABS(DER).GT.DERMAX) THEN
344             DERMAX=ABS(DER)
345             JDRMAX=J
346             ENDIF
347     C
348             IF(DER.EQ.0) THEN
349             N=N+1
350                IF(N.GT.LDER1) THEN
351                LDER1=N
352                JDER1=J
353                ELSE IF(N.GT.LDER2 .AND. ABS(J-JDER1).GT.NV/2-10) THEN
354                    LDER2=N
355                    JDER2=J
356                    ELSE IF(N.GT.LDER3) THEN
357                        LDER3=N
358                        JDER3=J
359                ENDIF
360             ELSE
361             N=0
362             ENDIF
363     420     CONTINUE
364     C
365     C
366             JDER1=JDER1-LDER1/2
367             JDER2=JDER2-LDER2/2
368             JDER3=JDER3-LDER3/2
369     C
370             IF(JDER3.EQ.0) JDER3=JDER2
371             IF(JDER2.EQ.0) JDER2=JDER1
372     C
373             WRITE(5,425) JDER1,JDER2,JDER3,DERMAX,JDRMAX
374     425     FORMAT(32H  JDER1 JDER2 JDER3  MAX.DER. **,3(I5),F9.1,I5)
375             A1=FF(JDER1)
376             A2=FF(JDER2)
377             A3=FF(JDER3)
378     C
379             IF(A1.GE.A2 .AND. A2.GE.A3) THEN
380             JA1=JDER1
381             JA2=JDER2
382             JA3=JDER3
383                ELSE IF(A1.GE.A3 .AND. A3.GE.A2) THEN
384                JA1=JDER1
385                JA2=JDER3
386                JA3=JDER2
387                    ELSE IF(A2.GE.A1 .AND. A1.GE.A3) THEN
388                    JA1=JDER2
389                    JA2=JDER1
390                    JA3=JDER3
```

```
391              ELSE IF(A2.GE.A3 .AND. A3.GE.A1) THEN
392              JA1=JDER2
393              JA2=JDER3
394              JA3=JDER1
395                ELSE IF(A3.GE.A1 .AND. A1.GE.A2) THEN
396                JA1=JDER3
397                JA2=JDER1
398                JA3=JDER2
399                  ELSE
400                  JA1=JDER3
401                  JA2=JDER2
402                  JA3=JDER1
403              ENDIF
404       C
405              IF(ABS(JA1-JDRMAX).GT.ABS(JA2-JDRMAX)) THEN
406                JAMP=JA1
407              ELSE IF(ABS(JA2-JDRMAX).GT.ABS(JA3-JDRMAX)) THEN
408                JAMP=JA2
409              ELSE
410                JAMP=JA3
411              ENDIF
412       C
413              AMPL=ABS(FF(JAMP))
414              WRITE(5,445) JAMP,AMPL
415   445        FORMAT(16H ** J   MAX-AMP**,I5,F9.1)
416       C
417       C ***
418              J1=0
419              J2=0
420              J3=0
421              L1=0
422              L2=0
423              L3=0
424              N=0
425              DO 840 J=1,NV
426              IF(FF(J).EQ.0) THEN
427              N=N+1
428                IF(N.GT.L1 .AND. J.LT.NV/4) THEN
429                L1=N
430                J1=J
431                ELSE IF(N.GT.L2 .AND. J.GT.NV/4) THEN
432                  L2=N
433                  J2=J
434                  ELSE IF(N.GT.L3) THEN
435                    L3=N
436                    J3=J
437                ENDIF
438              ELSE
439              N=0
440              ENDIF
441   840      CONTINUE
442       C
443              J1=J1-L1/2
444              J2=J2-L2/2
445              J3=J3-L3/2
446              IF(J1.EQ.0) THEN
447              J1=J2
448              L1=L2
449              ENDIF
```

```
450            IF(J2.EQ.0) THEN
451            J2=J1
452            L2=L1
453            ENDIF
454   C
455            WRITE(5,844) J1,L1,J2,L2,J3,L3
456   844      FORMAT(16H ZERO CROSSINGS*,6(I5))
457   C
458   C  *** FIND PHASE SHIFT
459   C
460            IF(FF(J1+L1)-FF(J1) .GT. 0) THEN
461            JPHASE=J1
462              ELSE IF(FF(J2)-FF(J2-L2).GT.0) THEN
463              JPHASE=J2
464                ELSE IF(FF(J3)-FF(J3-J3).GT.0) THEN
465                JPHASE=J3
466                   ELSE
467                   WRITE(5,666)
468   666             FORMAT(30H FAILURE IN PHASE DETECTION***)
469            ENDIF
470   C
471            PHASE=JPHASE*360./NV
472            WRITE(5,845) JPHASE,PHASE
473   845      FORMAT(15H JPHASE  PHASE*,I5,F9.1)
474   C
475            ANGU=2*PII/NV
476            PHASE=PHASE*PII/180
477            IF(PHASE.GT.PII) PHASE=2*PII-PHASE
478            DO 777 J=1,NV
479            FF(J)=AMPL*SIN(J*ANGU+PHASE)
480   777      CONTINUE
481   C
482            DO 89 J=1,NV
483            WRITE(5,893) NINT(FF(J))
484   893      FORMAT(10H AFT FFT**,I5)
485   89       CONTINUE
486   C
487   C
488   C
489   C  CORRECT RAW DATA ACCORDING TO SINE CURVE
490   C
491            DO 8900 I=1,NV
492            I2=I+1
493            I3=I+2
494            IF(I2.GT.NV) I2=NV
495            IF(I3.GT.NV) I3=NV
496            JDIF(I)=NINT((JDIF(I)+JDIF(I2)+JDIF(I3))/3.)
497   8900     CONTINUE
498   C
499            DO 8920 I=1,NV
500            JC(I)=65+FF(I)-JDIF(I)
501            WRITE(5,8915) I,JC(I)
502   8915     FORMAT(7H DIFF**,2(I5))
503            IF(ABS(JC(I)).LT.3) JC(I)=0
504   8920     CONTINUE
505   C
506            DO 99 I=1,NV
507            J1=JC(I)
```

```
508     C
509             IF(I.EQ.1) THEN
510             JBB=65+FF(2)-JDIF(2)
511             JBC=65+FF(3)-JDIF(3)
512               IF(ABS(JBB).LT.3) JBB=0
513               IF(ABS(JBC).LT.3) JBC=0
514                  IF(JBB.EQ.JBC .AND. J1.NE.JBB) J1=JBB
515             ENDIF
516             I0=I-1
517             I2=I+1
518             IF(I0.LT.1) I0=1
519             IF(I2.GT.NV) I2=NV
520             IF(JC(I0).EQ.JC(I2)) J1=JC(I0)
521     C
522             DO 90 J=1,128
523             FF2(J)=0
524             J2=J-J1
525             IF(J2.LT.1 .OR. J2.GT.128) GO TO 90
526             FF2(J)=FSIM(I,J2)
527  90         CONTINUE
528     C
529             DO 95 J=1,128
530             FSIM(I,J)=FF2(J)
531  95         CONTINUE
532     C
533     C
534  99         CONTINUE
535     C
536             INUM=0
537             JDIFCA=0
538     C
539             DO 922 I=1,NV
540             CMX=0
541             JX=1
542               DO 911 J=1,128
543               IF(ABS(FSIM(I,J)).GT.CMX) THEN
544               JX=J
545               CMX=ABS(FSIM(I,J))
546               JDIF(I)=JX
547               ENDIF
548  911          CONTINUE
549     C
550             JDIFCA=JDIFCA+JX
551  922        CONTINUE
552     C
553             JDIFCA=JDIFCA/NV
554             ISHI=65-JDIFCA
555     C        ISHI=0
556     C
557             WRITE(5,923) ISHI
558  923         FORMAT(8H SHIFT**,I5)
559     C
560             DO 924 J=1,128
561             FF(J)=0
562  924         CONTINUE
563     C
564             IF(ISHI.NE.0) THEN
565             DO 928 I=1,NV
```

```
566             DO 925 J=1,128
567             J2=J+ISHI
568             IF(J2.LT.1 .OR. J2.GT.128) THEN
569               FSIM(I,J)=0
570               GO TO 925
571             ENDIF
572             FF(J2)=FSIM(I,J)
573   925     CONTINUE
574             DO 927 J=1,128
575             FSIM(I,J)=FF(J)
576   927     CONTINUE
577   928     CONTINUE
578             ENDIF
579   C
580             RETURN
581             END
```

We claim:

1. A method for producing an image, the steps comprising:

acquiring a plurality of sets of raw profile data using an ultrasound reflection mode tomographic scan;

reconstructing a raw image using the acquired raw profile data sets;

locating an identification point in the reconstructed draw image;

calculating a corrective sinusoid which indicates a correct location of a signal produced by the identifiable point in each set of acquired profile data;

correcting each set of acquired profile data in the raw data set by shifting the set of acquired profile data in time by an amount necessary to place the actual signal produced by the identifiable point at the location indicated by the corrective sinusoid; and reconstructing an image using the corrected set of profile data.

2. The method as recited in claim 1 in which the corrective sinusoid is calculated using the expression:

$$S(i) = d \cos(\phi - \alpha)$$

Where:

d is the distance of the identifiable point from the center of rotation of the tomographic scan, $\phi$ is the angle of the identifiable point from the starting point of the tomographic scan, $\alpha$ is the angle at which each data profile is acquired during the tomographic scan.

3. The method as recited in claim 1 in which the identifiable point is the brightest point in the raw image and the highest amplitude peak in each set of acquired profile data is its corresponding signal.

4. The method as recited in claim 1, which further includes:

locating a second identifiable point in the reconstructed raw image;

calculating a second corrective sinusoid which indicates a correct location of a signal produced by the second identifiable point in each set of acquired profile data; and in which the correcting of sets of acquired profile data employs the actual signals produced by both identifiable points and both corrective sinusoids.

5. The method as recited in claim 1 in which the actual signal produced by the identifiable point is determined by detecting the maximum amplitude point in the set of acquired profile data.

6. The method as recited in claim 5 in which each set of acquired raw profile data is acquired as a signal which is rectified, filtered and stored in digitized form.

* * * * *